United States Patent [19]

Rabin et al.

[11] Patent Number: 5,200,318
[45] Date of Patent: Apr. 6, 1993

[54] DIAGNOSIS OF IDDM WITH A PANEL OF IMMUNOREAGENTS

[75] Inventors: Daniel U. Rabin, Branford; William J. Knowles, Madison, both of Conn.

[73] Assignee: Miles Inc., Elkhart, Ind.

[21] Appl. No.: 882,300

[22] Filed: May 13, 1992

[51] Int. Cl.$^5$ .............................................. C12Q 1/00
[52] U.S. Cl. ................................. 435/7.21; 435/4; 436/811
[58] Field of Search .................... 435/7.21, 4; 436/811

[56] References Cited

PUBLICATIONS

S. Baekkeskov et al., "Autoantibodies in Newly Diagnosed Diabetic Children Immunoprecipitate Human Pancreatic Islet Cell Proteins," Nature 298:167-169 (1982).

S. Baekkeskov et al., "Identification of the 64k autoantigen in insulin-dependent diabetes as the GABA-synthesizing enzyme glutamic acid decarboxylase," Nature 347 151-156 (1990).

S. Baekkeskov et al., "Antibodies to a 64,000 MW Human Islet Cell Antigen Precede the Clinical Onset of Insulin-dependent Diabetes," J. Clin. Invest. 79:926-934 (1987).

M. A. Atkinson et al., "Mr. 64000 Autoantibodies (64KA) Predict Insulin Dependent Diabetes," American Diabetes Assoc. 48th Annual Meeting (1988) Abstract #391.

M. A. Atkinson et al., "64000 Mr autoantibodies as predictors of insulin-dependent diabetes," The Lancet 335:1357-1360 (1990).

Gerling, I. et al. J. of Immunol. 137:3782-3785 (1986).

Christie, M. et al, Diabetologia 31:597-602 (1988).

D. U. Rabin et al, "Cloning and Expression of IDDM-Specific Human Autoantigens" Diabetes 41:183-186 (1992).

*Primary Examiner*—Sam Rosen
*Attorney, Agent, or Firm*—Andrew L. Klawitter

[57] ABSTRACT

Diagnosis of insulin-dependent (Type I) diabetes mellitus (IDDM) by contacting a blood sample from a patient with an immunoreagent comprising epitopes of two or more of glutamic acid decarboxylase (GAD) and the pancreatic islet cell antigens referred to as ICA512 and ICA12. Binding of antibodies present in the blood sample with one or more of such epitopes correlates with IDDM or a potential for developing IDDM. In clinical testing, about 80 percent of sera from newly diagnosed IDDM patients react positively with at least one epitope in a GAD/ICA512 panel. Reactivity with the GAD/ICA512/ICA12 panel is between about 80 and 90 percent. The method is useful in screening patients for pre-IDDM, for distinguishing IDDM from Type II diabetes, and for monitoring therapy.

21 Claims, 4 Drawing Sheets

DIAGNOSIS OF IDDM WITH A PANEL OF IMMUNOREAGENTS

BACKGROUND OF THE INVENTION

This invention relates to diagnosis of insulin-dependent (Type I) diabetes mellitus (IDDM) by detecting the presence of islet cell antibodies (ICAs) in a patient's blood sample. More particularly, the invention relates to a panel of immunoreagents for use in detecting ICAs as an indication of IDDM or a potential for developing IDDM.

The accumulating evidence of cellular and humoral abnormalities associated with IDDM has led to the hypothesis that the disease is an autoimmune disorder. Serum antibodies directed against the insulin-producing beta cells of the pancreatic islets have been detected by immunofluorescence, [G. F. Bottazzo, A. Florin-Christensen, and D. Doniach: Islet Cell Antibodies in Diabetes Mellitus With Autoimmune Polyendocrine Deficiencies, Lancet ii:1279-1283 (1974), and A. C. MacCuish, J. Jordan, C. J. Campbell, L. J. P. Duncan, and W. J. Irvine: Antibodies to Islet-cell in Insulin-dependent Diabetics With Coexistent Autoimmune Disease, Lancet ii:1529-1533 (1974)]. These autoantibodies are observed in 70-80% of newly diagnosed diabetics (NDD), but only in 0.1-1% of normal control subjects C. H. Brogren and A. Lernmark: Islet Cell Antibodies in Diabetes. Clin. Endocrinol. Metab. 11:409-430 (1982)], and G. F. Bottazzo, R. Pujol-Borrell, and D. Doniach: Humoral and Cellular Immunity in Diabetes Mellitus. Clin. Immunol. Allergy 1:139-159 (1981)]. ICAs have come to be accepted as one predictive factor for IDDM. A review of current knowledge on ICA is provided by A. Lernmark, Diabetic Medicine 4:285-292 (1987).

The conventional ICA assay consists of exposing pancreas sections to sera, staining with a second antibody bearing either a fluorescent [G. F. Bottazzo et al., supra] or enzyme label [P. G. Colman, M. Tatkus, A. Rabizadeh, C. Cahill, and G. S. Eisenbarth: Assay for Islet Cell Antibodies with Rat Pancreas and Peroxidase Protein A. Diabetes Care 11:367-368 (1988)], and observing under a microscope. Another similar method involves a biotin-avidin sandwich and immunofluorescent detection [T. Kobayashi, T. Sugimoto, T. Itoh, K. Kosaka, T. Tanaka, S. Suwa, K. Sato and K. Tsuju: The Prevalence of Islet Cell Antibodies in Japanese Insulin-dependent and Non-insulin-dependent Diabetic Patients Studied by Indirect Immunofluorescence and by a New Method. Diabetes 35:335-340 (1986)]. These methods are time consuming, laborious, difficult to reproduce, and have limited sensitivity. The development of a more convenient and sensitive immunoassay for ICA would permit widespread testing for epidemiology and correlation with IDDM, and ultimately prediction of the disease with a screening test.

A major limitation of current ICA tests is the limited knowledge and characterization of the islet cell antigens involved. The ICA's may be of low titer or affinity and approachable only with characterized antigens. ICA antigens that are detected by the immunofluorescence test are of special interest; these antigens may include:

(1) islet cell surface moieties [N. K. MacLaren, S. W. Hugng, and J. Fogh: Antibody to Cultured Human Insulinoma Cells in Insulin-dependent Diabetes. Lancet 1:997-1000 (1975), and A. Lernmark, Z. R. Freedman, C. Hofmann, A. H. Rubenstein, D. F. Steiner, R. L. Jackson, R. J. Winter and H. S. Traisman: Islet-cell-surface Antibodies in Juvenile Diabetes Mellitus. N. Engl. J. Med. 299:375-380 (1978)], (2) insulin [J. P. Palmer, C. M. Asplin, P. Clemons, K. Lyen, O. Tetpati, P. K. Raghu and T. L. Paquette: Insulin Antibodies in Insulin-dependent Diabetics Before Insulin Treatment. Science 222:1337-1339 (1983), and S. Srikanta, A. T. Ricker, D. K. McCulloch, J. S. Soeldner, G. S. Eisenbarth and J. P. Palmer: Autoimmunity to Insulin, Beta Cell Dysfunction, and Development of Insulin-dependent Diabetes Mellitus. Diabetes 35:139-142 (1986)], (3) glutamic acid decarboxylase; originally observed as a 64,000 dalton (64 kd) islet protein [S. Baekkeskov, J. H. Nielsen, B. Marner, T. Bilde, J. Ludvigsson, and A. Lernmark: Autoantibodies in Newly Diagnosed Diabetic Children Immunoprecipitate Human Pancreatic Islet Cell Proteins. Nature 298:167-169 (1982)], recent evidence indicates that this 64 kd protein is glutamic acid decarboxylase (GAD) [S. Baekkeskov, J-H. Aanstoot, S. Christgau, A. Reetz, M. Solimena, M. Cascalho, F. Folli, H. Richter-Olesen and P. DeCamilli: Identification of the 64 k autoantigen in insulin-dependent diabetes as the GABA-synthesizing enzyme glutamic acid decarboxylase. Nature 347:151-156 (1990)], (4) cytoplasmic antigens [G. F. Bottazzo, A. Florin-Christensen, and D. Doniach: Islet Cell Antibodies in Diabetes Mellitus With Autoimmune Polyendocrine Deficiencies. Lancet 2:1279-1283 (1974), A. C. MacCuish, J. Jordan, C. J. Campbell, L. J. P. Duncan, and W. J. Irvine: Antibodies to Islet-Cell in Insulin-Dependent Diabetics With Coexistent Autoimmune Disease. Lancet 2:1529-1533 (1974), R. Lendrum, G. Walker, and D. R. Gambli: Islet-Cell Antibodies in Juvenile Diabetes Mellitus of Recent Onset. Lancet 1:880-883 (1975), and W. J. Irvine, C. J. McCallum, R. S. Gray, G. J. Campbell, L. J. P. Duncan, J. W. Farguhar, H. Vaughan, and P. J. Morris: Pancreatic Islet Cell Antibodies in Diabetes Mellitus Correlated With The Duration and Type of Diabetes, Co-existent Autoimmune Disease, and HLA-type. Diabetes 26:138-147 (1977)], (5) glycoconjugates [R. C. Nayak, M. A. K. Omar, A. Rabizadeh, S. Srikanta, and G. S. Eisenbarth, "Cytoplasmic" Islet Cell Antibodies: Evidence That the Target Antigen is a Sialoglycoconjugate. Diabetes 34:617-619 (1985); P. Vardi, E. E. Dibella, T. J. Pasquarello, and S. Srikanta, Islet Cell Autoantibodies: Pathobiology and Clinical Applications Diabetes Care 10:645-56 (1987); B. K. Gillard, J. W. Thomas, L. J. Nell and D. M. Marcus, Antibodies Against Ganglioside GT3 in the Sera of Patients with Type I Diabetes Mellitus. Journal of Immunology 142:3826-32 (1989)].

Several reports indicate a high prevalence (ranging from 70% to 80%) of anti-64 kd antibody in prediabetic sera as well as newly diagnosed diabetic sera [S. Baekkeskov, M. Landin, J. K. Kristensen, S. Srikanta, G. Jan Bruining, R. Mandrup-Poulsen, C. de Beaufort, J. S. Soeldner, G. Eisenbarth, F. Lindgren, G. Sundquist, and A. Lernmark: Antibodies to a 64,000 MW Human Islet Cell Antigen Precede the Clinical Onset of Insulin-dependent Diabetes. J. Clin. Invest. 79:926-934 (1987), M. A. Atkinson, N. K. Maclaren, W. J. Riley, D. W. Sharp and L. Holmes: Mr 64,000 Autoantibodies (64KA) Predict Insulin Dependent Diabetes. American Diabetes Assoc. 48th Annual Meeting (1988) Abstract #391, M. A. Atkinson, N. K. Maclaren, D. W. Scharp, P. E. Lacy, and W. J. Riley: 64000 Mr autoantibodies as predictors of insulin-dependent diabetes. The Lancet 335:1357–1360 (1990), Baekkeskov, S. et al, Nature 298:167–169 (1982), Gerling, I. et al, J. of Immunol. 137:3782–3785 (1986), and Christie, M. et al, Diabetologia 31:597–602 (1988)].

Some other molecular species have been characterized by Western blotting as being "common antigens" recognized by diabetic sera [D. G. Karounos, V. J. Virta, L. J. Nell, and J. W. Thomas: Analysis of Human and RINm5F Islet Cell Antigens. American Diabetes Assoc. Res. Symp. Woods Hole, Mass. October 1987; Abstract #120]. These antigens have molecular weights of 150 kd, 84 kd, 60 kd, 49 kd, and 36 kd. A more recent report from the same laboratory indicates that there is a RIN antigen of Mr 52,000 that reacts with 29% of diabetic sera. [D. G. Karounos and J. W. Thomas: Recognition of Common Islet Antigen by autoantibodies From NOD Mice and Humans With IDDM. Diabetes 39:1085–1090 (1990), D. G. Karounos, L. J. Nell, and J. W. Thomas: Autoantibodies present at onset of type I diabetes recognize multiple islet cell antigens. Autoimmunity 6:79–91(1990), and D. G. Karounos, J. S. Wolinsky, B. K. Gillard, and J. W. Thomas: Molecular Mimicry in Type I Diabetes: An Antigenic Determinant on a Rubella Virus Protein is Shared with a 52 kD Beta Cell autoantigen. Diabetes 39:96A (1990)]. The first and third references indicate that the 52,000 antigen is RIN specific, not found in human islets or other tissue.

Very recently, two new islet cell protein antigens referred to as ICA12 and ICA512 have been identified, cloned, and found to be recognized specifically by sera from IDDM patients [D. U. Rabin, S. M. Pleasic, R. Palmer-Crocker, and J. A. Shapiro: Cloning and Expression of IDDM-Specific Human Autoantigens. Diabetes 41:183–186 (1992)].

Accordingly, the prevailing understanding is that multiple antigens exist which show some degree of reactivity with diabetic sera.

SUMMARY OF THE INVENTION

It has now been found that a panel of ICA epitopes from two or more of glutamic acid decarboxylase (GAD) and the pancreatic islet cell antigens referred to as ICA12 and ICA512 provides a means for detecting and/or monitoring IDDM of improved sensitivity. In particular, it has been found that about 80 percent of sera from newly diagnosed IDDM patients contain ICAs reactive with one or both of epitopes from GAD and ICA512, with between about 80 and about 90 percent of sera showing reactivity with the three member panel of GAD/ICA512/ICA12. The subsets of sera recognized by the three antigens are independent. In individual testing, the percentages of positive results are only in the range of 63 percent for GAD, 55 percent for ICA512, and 32 percent for ICA12.

The present method is useful in several different aspects in the diagnosis of IDDM. In particular, the present method is useful in screening of patients from the general population, particularly juveniles, wherein a positive test result (i.e., a finding that a patient's blood contains antibodies that bind to at least one of the ICA antigen panel) indicates that such patient is at risk to develop IDDM, that is, that such patient may have a pre-IDDM condition. Furthermore, the present method is applicable to the screening of first degree relatives (i.e., siblings and children) of individuals already diagnosed as having IDDM. Patients with positive test results from the subject ICA panel would likely be examined in more detail, including the performance of metabolic and genetic testing, to determine whether glucose intolerance has already occurred, or whether additional risk factors are present.

Other applications of the present method include the testing of a patient already diagnosed with diabetes for the purpose of determining if IDDM is involved, for instance in the case of a Type II diabetic who may also experience the onset of IDDM. The detection of IDDM or pre-IDDM would have therapeutic implications in such a situation. Furthermore, the present method is useful in the monitoring of diabetic therapy, particularly in regard to immunosuppressant therapy. It is also contemplated that, as a multiparameter test, antigen profiles would be useful in predicting the course or severity of the disease, response to particular therapies, and/or risk for particular complications.

DESCRIPTION OF THE PREFERRED EMBODIMENTS

Figure 1:
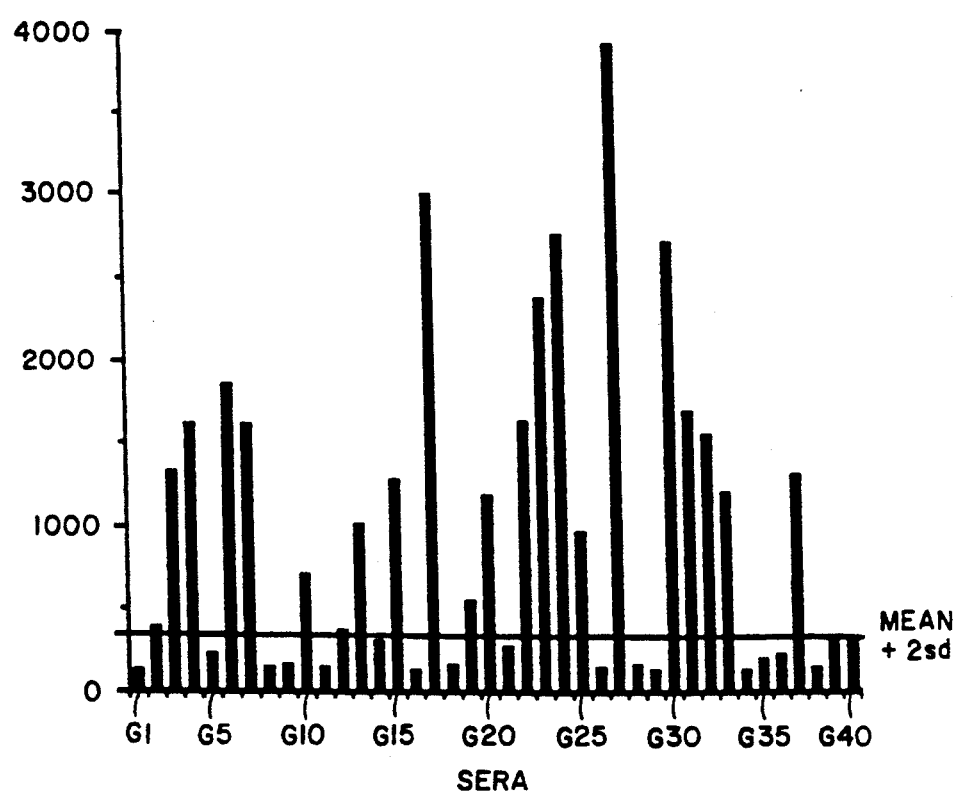
FIGS. 1, 2, and 3 are bar graphs showing relative reactivities of sera from 40 newly diagnosed diabetics with GAD, ICA12, and ICA 512, respectively.

As used herein, the term "ICA epitopes or antigens" shall be understood to refer individually and collectively to "GAD epitopes or antigens", "ICA512 epitopes or antigens", and "ICA12 epitopes or antigens", and shall mean immunoreagents in the form of proteins, polypeptides, or peptides to which islet cell antibodies found in the sera of newly diagnosed IDDM patients will bind. Where such terms are used, it will be understood that in some cases peptide forms will not be "antigens" in the strictest sense, i.e., they would be haptenic since they would require attachment to a conventional macromolecular carrier in order to stimulate the production of antibodies in a host animal. Further, anti-idiotypic antibodies, or fragments thereof comprising an antibody combining site (e.g., Fab, Fab', or F(ab')$_2$), having the binding characteristics of ICA epitopes will be considered to be equivalents to such epitopes for the purposes of the present invention.

Preparation of GAD

As used herein, "GAD" shall mean the protein glutamic acid decarboxylase, whether derived by isolation or purification from a biological source or by expression of a cloned gene encoding GAD, and fragments of any such protein, including fragments obtained by digestion of the protein or a portion thereof, fragments obtained by expression of a gene coding for a portion of the GAD protein, and synthetic peptides having amino acid sequences corresponding to a portion of the GAD protein. The aforesaid fragments of the GAD protein will normally comprise a sequence of at least 4, and more commonly at least 6, amino acids corresponding to a portion of the sequence of the GAD protein.

Glutamic acid decarboxylase can be isolated, cloned, or otherwise obtained from a variety of sources and in a variety of isoforms. Typically, GAD is derived from mammalian (e.g., porcine, murine, feline, or human) brain or pancreatic tissue. Methods for biochemical isolation of such material from natural sources, e.g., rat brain or porcine brain, are found in the literature [see, for example, D. Gottlieb, Y.-C. Chang, and J. Schwob, Proc. Natl. Acad. Sci. 83:8808–8812 (1986), and Y.-C. Chang and D. Gottlieb, J. of Neuroscience 8(6):2123–2130 (1988)].

Isolation of GAD from biological material usually will involve purification by conventional techniques such as chromatography, particularly affinity chromatography. Purified GAD can be used to prepare antibodies of polyclonal or monoclonal type which can then be used in affinity purification according to conventional procedures. Resulting purified GAD material can be further processed, e.g., fragmented, by chemical or enzymatic digestion. Useful fragments will be identified by screening for desired reactivity with diabetic sera.

GAD epitopes can also be prepared by expression of recombinant DNA clones coding for GAD or a portion thereof. The cloned GAD gene may itself be natural or synthetic, with the natural gene obtainable from cDNA or genomic libraries using oligonucleotide, DNA fragment, or antibody probes [J. Sambrook, E. F. Fritsch, and T. Maniatis (1989) Molecular Cloning: A Laboratory Manual, Cold Spring Harbor Press]. Other techniques for obtaining suitable recombinant DNA clones, as well as methods for expressing the cloned gene, will be evident to the worker in the field. It has been shown that there are at least two forms of GAD, referred to as GAD65 and GAD67, that derive from distinct genes [M. G. Erlander, N. J. K. Tillakaratne, S. Feldblum, N. Patel, and A. J. Tobin (1991) Neuron 7:91–100].

Preparation of ICA512 and ICA12

As used herein, "ICA512" and "ICA12" shall mean a protein or polypeptide consisting of or comprising the polypeptides encoded by the cDNA inserts in deposited recombinant phages ATCC 40706 and 40550, respectively, and fragments of such proteins and polypeptides, including fragments obtained by digestion of such protein and polypeptides, fragments obtained by expression of a gene coding for a portion of any such protein or polypeptide, and synthetic peptides having amino acid sequences corresponding to such proteins or polypeptides or a portion thereof. The aforesaid fragments of the ICA512 or ICA12 polypeptides will normally comprise a sequence of at least 4, and more commonly at least 6, amino acids corresponding to a portion of the sequence of such polypeptides, respectively.

ICA512 and ICA12, as defined herein, can be prepared in a number of different ways from the clones and sequence information provided by the present invention. Further information regarding the preparation and characterization of ICA512 and ICA12 is provided in U.S. patent application Ser. No. 715,181, filed Dec. 4, 1989, entitled "Pancreatic Islet Cell Antigens Obtained By Molecular Cloning" (Docket No. MSE-251.2), and commonly assigned with the present application. One can simply express the proteins from the ATCC deposited clones. Such expressed proteins, or fragments or digestion products thereof, can be used as antigens for binding to islet cell antibodies. However, direct use of bacterial expression extracts may not be possible in some cases since human sera normally react nonspecifically with E. coli proteins. In such cases, the expressed ICA antigens can be isolated by conventional techniques such as electrophoretic separation followed by immobilization on membranes (Western blotting), or by column chromatography or affinity purification (e.g., anti-beta-galactosidase affinity resin chromatography or other conventional biochemical means, e.g., salt or temperature precipitation).

Fragments can be obtained by expression of partial clones or by proteolytic or other forms of digestion, followed by isolation and screening of fragments for those of desired reactivity with diabetic sera. Alternatively, peptide fragments can be synthesized by well-known methods from the amino acid sequences deduced from experimentally determined DNA sequences of ICA512 and ICA12. Overlapping peptides can be synthesized and tested for reactivity with ICA sera. As reactive peptides are found, smaller peptides can be prepared in order to map the smallest reacting unit, i.e., the epitope.

Furthermore, fragments of the cDNA inserts of ATCC 40706 and 40550, respectively, can be used to isolate full-length cDNA or genomic DNA clones from appropriate libraries by standard methods. Proteins and polypeptides encoded by such full-length cDNA or genomic DNA, or fragments thereof, can be expressed and screened for utility as ICA512 and ICA12 immunoreagents in the present invention. Furthermore, fragments of such expressed proteins and polypeptides, e.g., obtained by digestion or as synthetic peptides prepared from deduced amino acid sequences, can be also be screened for utility as ICA512 and ICA12 immunoreagents.

Full-length cDNA or genomic DNA clones can be isolated in the following manner. The target library is spread on plates, allowed to grow, transferred to filters, and reacted with DNA probes. Such DNA probes are generated from restriction fragments of the cDNA inserts by such methods as end labeling, nick translation, random primed transcription, or photochemical means. Oligonucleotides can be synthesized, labeled, and used as hybridization probes. RNA probes can also be generated from subcloned cDNA by transcription from appropriate templates.

Recombinant cloning vehicles, e.g., phage or plasmids, that appear to react with the partial cDNA clones are re-screened and then restriction mapped. Promising clones are then sequenced to confirm the hybridization of the original probes and to obtain extended sequence information on the larger fragment. If full-length clones are not obtained in this procedure, the complete sequence of the nucleic acid coding for the human gene can be pieced together from overlapping sequences of cloned fragments.

An alternative method for obtaining longer fragments, and possibly full-length clones, uses antibodies raised against ICA antigens expressed by partial clones. After identifying an antigen of interest, it can be used as an immunogen to raise monoclonal or polyclonal antibodies of high titer and affinity. Such antibodies will enable the detection of longer cDNA clones and cDNA clones present in lower amounts in the library.

Immunoreagent and Immunoassay Methods

The immunoreagent employed in the present invention can be in a variety of forms. The essential feature is the ability to determine binding of antibodies from a blood sample to either or both of the ICA epitopes when a two antigen panel is used (e.g., GAD and ICA512) or, in the case of using the three antigen panel, binding to one or more of GAD, ICA512, and ICA12), as defined herein. It will be evident to one of ordinary skill in the art that such feature can be obtained by a variety of means. For example, the antigen panel (e.g., comprising GAD/ICA512 or GAD/ICA512/ICA12) can comprise individual test components or can be combined in a single test component. For the general diagnosis or monitoring of IDDM, it is not necessary to determine which particular antigen or antigens in the panel react with a blood sample of a particular patient. Binding to any one of the members of the panel indicate a positive result. Accordingly, it is generally not necessary to prepare the immunoreagent in a form in which the GAD, ICA12, and ICA512 epitopes are physically isolated or separable.

The present method, in general, comprises contacting or otherwise reacting a patient's blood sample, normally a serum sample, with the subject ICA antigen panel and determining immunoreactivity by any conventional technique. A wide variety of immunoassay methodologies and formats are available from which the skilled worker can choose. Representative examples of just a few of the many techniques that can be applied to the detection of immunoreactivity of a test sample with the ICA antigen panel of the present invention are provided below.

Particularly useful immunoassay formats employ a combination of solid phase or immobilized reagents and labeled reagents whereby the association of the label with the solid phase is a function of the presence or absence of reactivity with the panel antigens. In general, such a solid phase reagent comprises a binding substance such as a member of the antigen panel, an anti-antibody (e.g., anti-IgG), or other immunobinder or other binding agent according to the assay protocol involved, bound or attached, covalently or noncovalently, to a solid phase matrix or in an otherwise immobilized form. Useful solid phase matrices are conventional in the art and include such matrices as microtiter plate wells, test tubes and other test containers or vessels, test strips, beads, and particles such as plastic microparticles and latexes. Where a solid phase reagent comprises the antigen panel of the present invention, it will be recognized that each such antigen or epitope comprised in the panel can be physically separated or isolable from the others or two or more can be mixed or otherwise associated in an undifferentiated manner with the solid phase. For example, panel members can be immobilized in separate wells of a microtiter plate or can occupy the same wells; or, where the solid phase is in the form of particles, each individual particle can have attached only a single panel member, or can have attached two or more or all of the panel members.

Similarly, useful labeled reagents comprise a binding substance such as a member of the antigen panel, an anti-antibody (e.g., anti-IgG), or other immunobinder or other binding agent according to the assay protocol involved, which is chemically coupled with a detectable chemical moiety. Useful labels are conventional in the art and include fluorescers, chemiluminescers, radioisotopes, and enzymes. Enzyme labels are particularly useful and are generally selected from alkaline phosphatase, peroxidase, and $\beta$-galactosidase. Enzyme labels are readily detectable by addition of a corresponding chromogenic substrate and detecting the resulting color or fluorescent response.

One particular immunoassay format that can be applied to the present method employs an immobilized form of the antigen immunoreagents. A test sample is incubated with the solid phase antigen and preferentially washed to remove unbound material. A labeled antibody reagent is then added. Such antibody reagent can be specific for a particular class of immunoglobulin, e.g., IgG, IgM, IgA, etc., or can be a mixture of conjugates so that all immunoglobulin types are detectable. Islet cell antibodies of interest are generally of the IgG isotype and thus anti-IgG would normally be employed. The solid phase is washed to remove unbound labeled antibody reagent and the label activity remaining on the solid phase is measured qualitatively or quantitatively.

A variation of this protocol uses a ligand-modified form of the antigen(s) with immobilization to the solid phase being accomplished by using a solid phase bearing a binding partner to the ligand. For example, biotin or a hapten (e.g., fluorescein) can be used as the ligand and can be rendered immobilized by contact with a solid phase form of avidin or anti-hapten antibody, respectively. The addition of the solid phase binding partner can occur at any convenient time in the assay, such as prior to contact of sample with the ligand-antigen(s) or thereafter.

Another immunoassay format that can be applied to the present method employs an immobilized form of an antibody reagent. Antibody specific for the desired ICA immunoglobulin type to be detected (e.g., IgG), or a mixture of antibodies against different IgG isotypes, is immobilized on a solid phase and incubated with the test sample. Resulting islet cell antibody that has become bound to the solid phase antibody reagent can then be detected in several different manners. For instance, one can add labeled forms of the antigen panel, either as individually labeled reagents or as a combined labeled reagent. Or, one can add a soluble form of the antigen panel and then, together in the form of a complex, or later as a separate reagent addition, labeled antibody that can bind with the antigen reagents. Further, one can add a soluble form of the antigen panel which has been modified with a ligand and then adding a labeled form of a binding partner to the ligand. The previously described variation of using a ligand-modified form of the solid phase reagent, in this case, antibody, with immobilization to the solid phase being accomplished by using a solid phase bearing a binding partner to the ligand, can also be used.

A competitive immunoassay format is also useful. Immobilized antigen is employed along with a labeled form of islet cell antibodies. Labeled antibody and ICA from the test sample are allowed to compete for binding to the immobilized antigen panel either simultaneously or sequentially, e.g., by exposing the solid phase antigen panel first to the sample and thereafter to the labeled antibody reagent. Again, as above, the solid phase antigen can be immobilized directly to the solid phase or through a ligand-binding partner bridge as described above, with the immobilization step being performed at any convenient time in the assay, including as the last step.

Latex or particle agglutination methods are also to be mentioned. Particles are coated or covalently coupled with antigen. The antigen particles are then incubated with the test sample and resulting agglutination of the particles due to the formation of ICA antibody linkages between particles is detected. Detection can be accomplished by visual observation (a slide agglutination format) or quantitated by measuring turbidity changes with a spectrophotometer or nephelometer. A variation is based on inhibition of particle agglutination. Each particle reagent comprises one or more monoclonal antibodies corresponding specifically with one or more particular antigens, respectively. In addition, an agglutinator reagent is prepared comprising multiple antigens, e.g., a water soluble polymer backbone to which are attached multiples of one or more of the antigen panel. When mixed with sample, the absence of ICA in the sample results in agglutination of the particles by formation of bridges formed by the agglutinator reagent. When ICA is present, it binds to the agglutinator and thereby prevents or inhibits agglutination.

The present invention will now be illustrated, but is not intended to be limited, by the following examples.

EXAMPLES

Expression of ICA12 and ICA512. The EcoRI insert from λgt11 clone ATCC 40706 was subcloned into pBluescript KS (Strategene, LaJolla, Calif., USA) and subsequently into a modified version of plasmid pGEX (Pharmacia, Piscataway, N.J., USA) for expression and purification as a glutathione-S-transferase (GST) fusion protein. This modified vector, pGEXc, was adapted for expression of λgt11 restriction sites. The expressed fusion of GST and ICA512 (GST512) was purified on a glutathione (GT) column and cleaved with thrombin [D. B. Smith and K. S. Johnson (1988) Single-step purification of polypeptides expressed in Escherichia coli as fusions with glutathione-S-transferase. Gene 67:31–40; and F. G. C. Abath and A. J. G. Simpson (1991) A simple method for the recovery of purified recombinant peptides cleaved from glutathione-S-transferase-fusion proteins. Biotechniques 10:178]. ICA512 was separated from GST by rechromatography on GT-Sepharose.

The EcoRI insert from λgt11 clone ATCC 40550 was subcloned and expressed in the same way. It was found that the fusion protein and the cleaved ICA12 gave similar ELISA results, so the fusion protein (GST12) was used.

GAD Purification. Porcine brain (150g) was homogenized for 30 minutes (0° C.) in 1L of 5 mM EDTA, 1 mM 2-aminoethylisothiouronium bromide (AET), 0.1 mM phenylmethylsulfonylfluoride (PMSF), 20 μM pyridoxal phosphate, and 20 μM leupeptin. The homogenate was centrifuged at 20,000×g for 45 minutes at 4° C. and the pellet discarded. The supernatant was centrifuged at 100,000×g for 45 minutes at 4° C. and the pellet again discarded. The supernatant containing GAD was loaded onto a 5 ml Sepharose CL-4B column containing 10 mg of the monoclonal antibody GAD1 (Gottlieb et al, PNAS 83:8808, 1986). The column was washed with 100 ml of 50 mM potassium phosphate, 1 mM AET, 20 μM pyridoxal phosphate, pH 7.2 followed by 20 ml of the above solution containing 1M sodium chloride. The bound GAD was eluted with 50 mM potassium phosphate, 10 mM diethylamine, 20μM pyridoxal phosphate, 1 mM AET and 20 mM glutamic acid, pH 10.5. The fractions were immediately neutralized with a 1/10 volume of 1 M sodium phosphate, pH 6.9. All fractions were assayed for enzyme activity and analyzed by SDS gel electrophoresis. Fractions containing GAD were pooled and used in the immunoprecipitation assay described below.

ELISA with ICA12 and ICA512. 30 ng of cleaved and purified ICA512 was deposited in each well of an Immulon-2 microtiter plate (Dynatech, Chantilly, Va.) in TBS buffer (20 mM Tris pH 8.0, 150 mM NaCl) and allowed to stand overnight at room temperature. The plate was blocked with a blotto/Tween-20 (5% Carnation non-fat dry milk, 10 mM Tris pH 8.0, 150 mM NaCl, 0.05% Tween-20, and 0.05% sodium azide) solution for one hour, and then reacted in duplicate with 1.5 μl of human serum diluted in 50 μl blotto/Tween for one hour. After washing five times with PBS/Tween, the wells were incubated with 100 μl of a 1/1000 dilution of alkaline phosphatase (AP) conjugated anti-human IgG antibody (Sigma A-0287) for one hour. After washing 5 times in PBS/Tween and once for 15 minutes with TBS/Tween, the plate was developed with nitrophenylphosphate (1 Sigma tablet #104–105 in 10 ml of 1M diethanolamine, 0.5 mM $MgCl_2$ pH 9.8) for 1–2 hours. Optical density was read at 405 nm in a $V_{max}$ plate reader (Molecular Devices, Menlo Park, Calif, USA). The type of plate, the amount of antigen and serum, the blocking reagent, the detecting antibody, and the incubation times were selected to optimize the signal/noise ratio as well as to conserve reagents.

GST12 ELISA measurements were done identically except that 35 ng of protein was coated on Immulon-1 plates in EIA buffer (0.1M bicarbonate pH 9.5).

Serum. Diabetic sera and plasma samples were obtained from juvenile onset diabetic subjects by the University of Missouri Medical Center, Columbia with informed consent. Most samples were collected before therapy, and all were collected within two weeks of diagnosis. Control samples were obtained from the clinical lab of the Children's National Medical Center in Washington, DC and from healthy adults.

GAD Radiolabeling and Immunoprecipitation. Porcine GAD purified as above was iodinated using the Bolton Hunter chemistry. Typically 1 μg of GAD in 50 μl of 0.1M sodium bicarbonate pH 8.5, was added to 1 mCi of $N_2$ dried Bolton Hunter reagent (Amersham IM5861X, Amersham, Arlington Heights, Ill., USA) and reacted on ice for 15 minutes. The reaction was terminated by the addition of 25 μl 1M glycine, pH 8.5 and the unincorporated label separated from GAD by gel filtration on Sephadex G25 using PBS containing 0.1% gelatin.

The labeled GAD was preabsorbed with normal sera prior to use in the immunoprecipitation assay.

Typically a pool of 4 normal sera (125 μl) was added to $1 \times 10^6$ cpm GAD (the amount necessary for 10 single measurements) and the incubated on ice for 60 minutes. A 50% slurry (250 μl) of Protein A-Sepharose CL-4B was added and the mixture incubated on ice for 60 minutes. The fluid phase was collected by centrifugation through a filter and subsequently used in the immunoassay.

For the detection of anti-GAD antibodies, 12.5 μl of sera was premixed with an equal volume of a protease inhibitor cocktail (benzamidine, PMSF, aprotinin, pepstatin A, p-chloromercuriphenylsulfonic acid in 20 mM Tris, 150 mM NaCl containing 0.5% (w/v) Triton-100, pH 7.4. An aliquot of the preadsorbed GAD was then added to the serum-inhibitor cocktail and incubated overnight at 4° C. 25 μl of the 50% Protein A-Sepharose slurry was then added and incubated for 60 minutes. The Protein A-Sepharose is washed 5 times by brief centrifugation and resuspension in the above buffer minus the protease inhibitors. The final pellet was counted in a gamma counter or the bound GAD solubilized in SDS and analyzed by conventional procedures of electrophoresis, autoradiography and film scanning.

Figure 2:
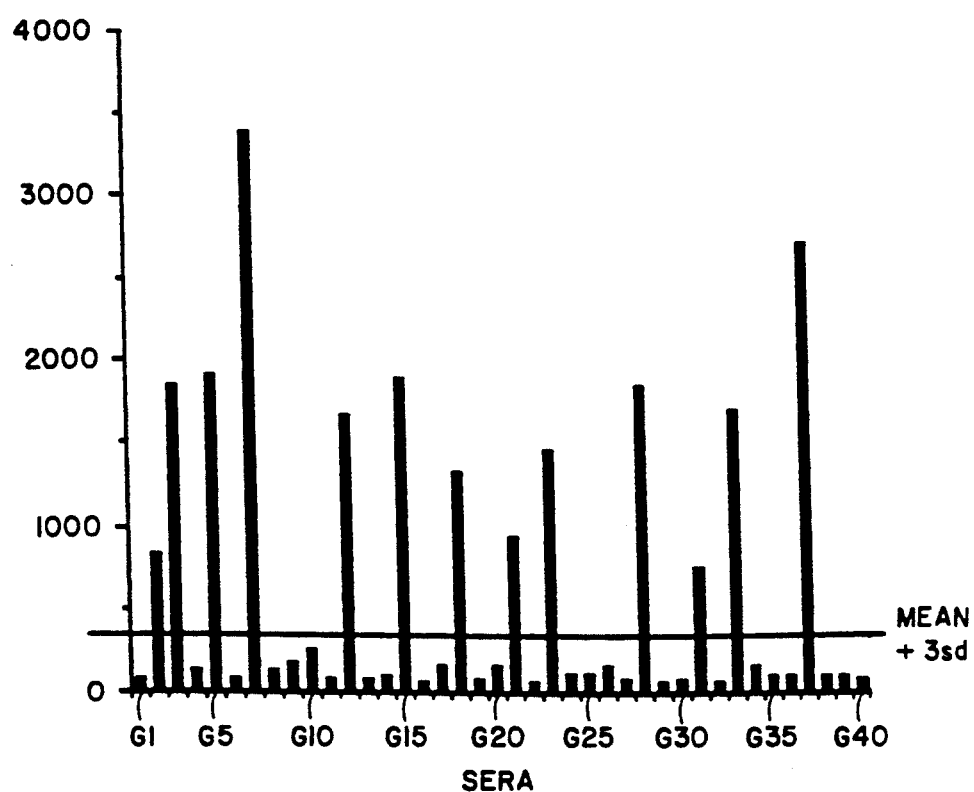
Figure 3:
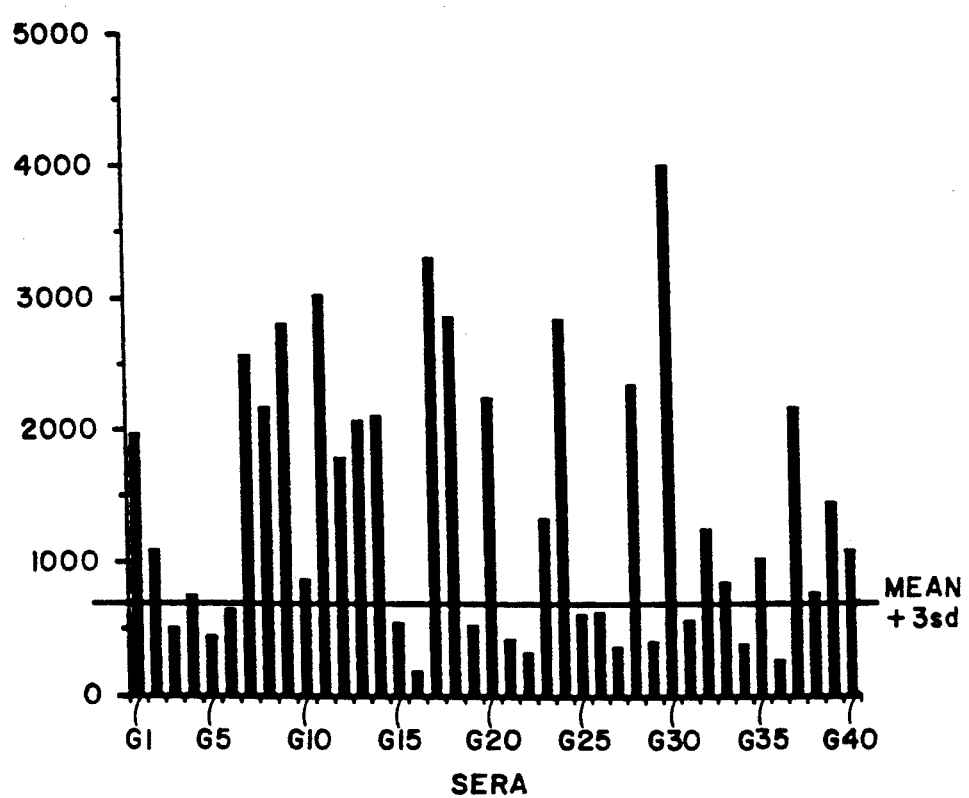
Figure 4:
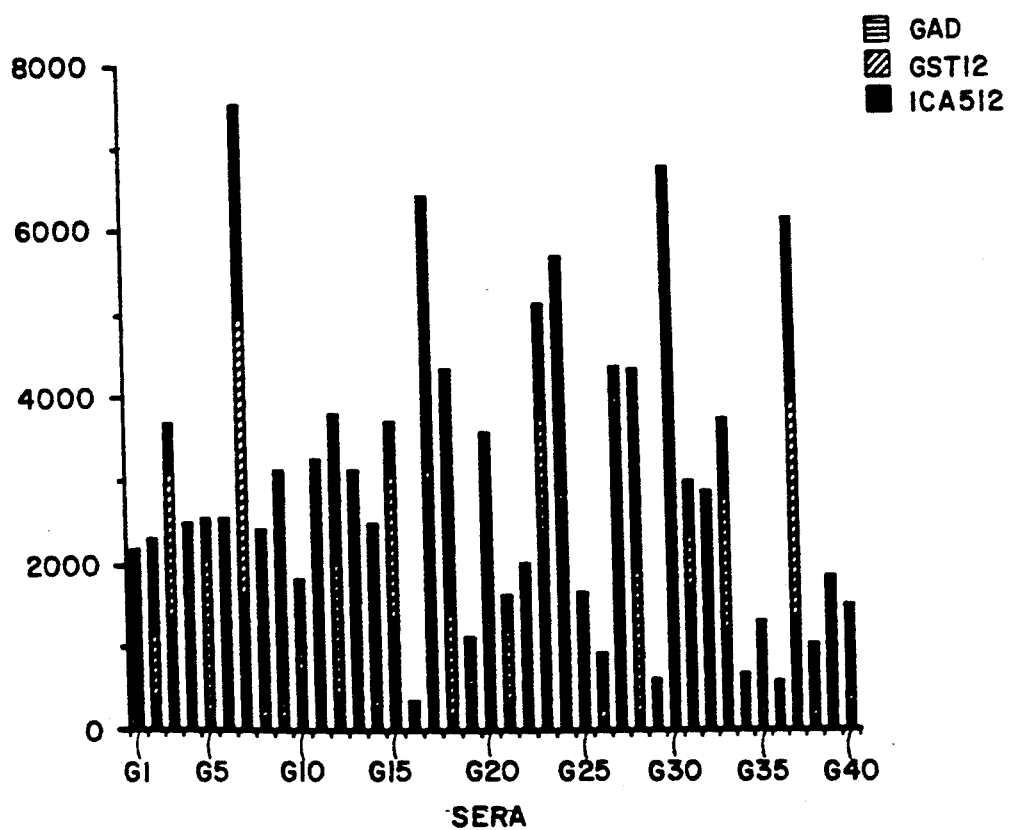
FIGS. 4 is a bar graph showing the combined relative reactivities of the same 40 diabetic sera with the three ICA antigens.

Results. The results presented in FIGS. 1–3 show that the three antigens ICA512, ICA12, and GAD react with 53%, 26%, and 62%, respectively, of a panel of 40 newly diagnosed diabetic sera and plasma samples (some of the panel members are duplicates, one sample being a serum sample and the other a plasma sample—the duplicate pairs are 1 & 11, 2 & 12, 3 & 15, 5 & 21, 6 & 32, and 7 & 37). FIG. 4 is a graphic summary of the reactivities. Some samples (G2 & G12, G7 & G37, G23, and G33) react with all 3 antigens, while 5 of the samples (G16, G26, G29, G34 and G36) react with none of them. The other samples react with one or several but not all. Counting each of the duplicates as an individual sample, 82% of the samples react with one or both of GAD and ICA512, 68% react with one or both of GAD and ICA12, 62% react with one or both of ICA512 and ICA12, while 85% of the samples react with at least one of the GAD/ICA512/ICA12 antigens. In a screening situation, such criterion would be grounds for further testing and suspicion that the positive individual is a pre-diabetic.

The present invention has been particularly described and exemplified above. It is contemplated that many other variations and modifications of the invention can be made without departing from the spirit and scope hereof.

"ATCC 40550" and "ATCC 40706" are the designations given by the American Type Culture Collection, Rockville, Md., USA, for recombinant phages referred to hereinabove. These biological cell deposits were made Feb. 8, 1989, and Nov. 14, 1989, respectively in accordance with the Budapest Treaty.

What is claimed is:

1. A method for the diagnosis of insulin dependent diabetes mellitus in a patient, comprising the steps of contacting a blood sample obtained from such patient with an immunoreagent comprising epitopes of two or more of GAD, ICA512, and ICA12, and determining binding of antibody present in the patient's blood sample to one or more of said epitopes.

2. The method of claim 1 wherein said epitopes include an epitope of GAD.

3. The method of claim 2 wherein said GAD is isolated from a mammalian source.

4. The method of claim 3 wherein said biological source is porcine brain.

5. The method of claim 2 wherein said GAD is a recombinantly expressed polypeptide or a fragment thereof.

6. The method of claim 1 wherein said ICA512 and/or ICA12 is a recombinantly expressed polypeptide or a fragment thereof.

7. The method of claim 1 wherein said ICA512 and/or ICA12 immunoreagent is a synthetic peptide.

8. The method of claim 1 wherein the patient is a member of the general population and a positive test result indicates that such patient is at risk to develop IDDM.

9. The method of claim 1 wherein the patient is a first degree relative of an individual with IDDM and a positive test result indicates that such patient is also at risk to develop IDDM.

10. The method of claim 1 wherein the patient is a diabetic and a positive test result indicates that such patient's diabetes is IDDM.

11. The method of claim 1 wherein said immunoreagent comprises epitopes of GAD and ICA512.

12. The method of claim 1 wherein said immunoreagent comprises epitopes of all three of GAD, ICA512, and ICA12.

13. A test kit for use in the diagnosis of insulin dependent diabetes mellitus in a patient, comprising one or more containers holding an immunoreagent comprising epitopes of two or more of GAD, ICA512, and ICA12.

14. The test kit of claim 13 wherein said epitopes include an epitope of GAD.

15. The test kit of claim 14 wherein said GAD is isolated from a biological source.

16. The test kit of claim 15 wherein said biological source is porcine brain.

17. The test kit of claim 14 wherein said GAD is a recombinantly expressed polypeptide or a fragment thereof.

18. The test kit of claim 13 wherein said ICA512 and/or ICA12 is a recombinantly expressed polypeptide or a fragment thereof.

19. The test kit of claim 13 wherein said ICA512 and/or ICA12 is a synthetic peptide.

20. The test kit of claim 13 wherein said immunoreagent comprises epitopes of GAD and ICA512.

21. The test kit of claim 13 wherein said immunoreagent comprises epitopes of all three of GAD, ICA512, and ICA12.

* * * * *